US008969408B2

(12) United States Patent
Hwang et al.

(10) Patent No.: US 8,969,408 B2
(45) Date of Patent: Mar. 3, 2015

(54) USE OF LIGNAN-TYPE COMPOUNDS OR EXTRACT OF NUTMEG OR ARIL OF NUTMEG COMPRISING THE SAME (75) Inventors: Jae Kwan Hwang, Kyeonggi-Do (KR); Yu-Mi Cho, Seoul (KR); Gyu Hoi Kim, Paju Gyeonggi-Do (KR); Jeong Hwan Kim, Seoul (KR); Hae Ji Lee, Incheon (KR); Do Un Kim, Gyeonggi-Do (KR); Hee Chul Chung, Seongnam Gyeonggi-Do (KR); Jae Youn Chung, Gyeonggi-Do (KR); Hyun In Oh, Suwon Gyeonggi-Do (KR)

(73) Assignees: Biocare Co., Ltd., Seoul (KR); Newtree Co., Ltd., Sungnam, Gyeonggi-do (KR)

( * ) Notice: Subject to any disclaimer, the term of this patent is extended or adjusted under 35 U.S.C. 154(b) by 671 days.

(21) Appl. No.: 12/738,626

(22) PCT Filed: Oct. 17, 2008

(86) PCT No.: PCT/KR2008/006143
§ 371 (c)(1),
(2), (4) Date: Dec. 20, 2010

(87) PCT Pub. No.: WO2009/051437
PCT Pub. Date: Apr. 23, 2009

(65) Prior Publication Data
US 2011/0118346 A1    May 19, 2011

(30) Foreign Application Priority Data

Oct. 17, 2007   (KR) .................. 10-2007-0104783

(51) Int. Cl.
*A61K 31/36*     (2006.01)
*A61K 31/34*     (2006.01)
*A61Q 19/02*     (2006.01)
*A61K 8/49*      (2006.01)
*A61K 8/97*      (2006.01)

(52) U.S. Cl.
CPC .............. *A61Q 19/02* (2013.01); *A61K 8/4973* (2013.01); *A61K 8/97* (2013.01)
USPC .......................................... 514/464; 514/473

(58) Field of Classification Search
None
See application file for complete search history.

(56) References Cited

U.S. PATENT DOCUMENTS

2009/0192217 A1*   7/2009 Hwang et al. ................ 514/464

FOREIGN PATENT DOCUMENTS

| JP | 8-157347 A | 6/1996 |
| JP | 2005-289838 A | 10/2005 |
| KR | 10-2004-0092782 | 11/2004 |
| KR | 10-2005-0073027 | 7/2005 |

OTHER PUBLICATIONS

Abu All Ibn-e-Sina; Al-Qaanoon-fil-Tibb, vol. II (11th century AD), Institute of History of Medicine and Medical Research, Jamia Hamdard, New Delhi-62, 1987 AD, p. 124, Formulation Id: AH1/171 Formulation Name: Jauzbuwa, Publication (Prior art): p. No. 16, English Translation including Terminology Conversion (TKDL Extracts): p. No. 17.

Bharata Bhaisajya RatnAkara—Compiled by Naglnadaisa Chaganalala ,Translated by Gopinath Gupta—vol. IV : B. Jain Publishers, New Delhi, Edn. 2nd. Reprint, Aug. 1999. [This book contains back references from 1000 B.C.to 20th century], p. 143, Formulation Id: RS/426, Formulation Name: Mukhakantikardlepah (13), Publication (Prior art):p. No. 10, English Translation including Terminology Conversion (TKDL Extracts): p. No. 11.

Bharata Bhaisajya Ratnalara—Compiled by Naglnadasa Chaganalala Naha ,Translated by Gopinath Gupta—vol.-II : B. Jain Publishers, New Delhi, Edn. 2nd. Reprint, Aug. 1999. [This book contains back references from 1000 B.C.to 20th century], p. 269 Formulation Id: BP/958, Formulation Name: ratlpatradilepah, Publication (Prior art):p. No. 06, English Translation including Terminology Conversion (TKDL Extracts): p. No. 07.

BhavamiSra; Bhavaprakaga—Edited & translated by Brahmasankara Misra, Part-II : Chaukhamba Sanskrit Sansthan, Varanasi, Edn. 7th, 2000. [Time of origin 16th century], p. 589; Formulation Id: RG/2838A; Formulation Name: Jatphalalepah; Publication (Prior art):p. No.03; English Translation including Terminology Conversion (TKDL Extracts): p. No. 04-05.

Mohammad Najmul Ghani Khan; Khazaain-al-Advia, vol. II (20th century AD), Nadeem Yunus Printer / Sheikh Mohd Basheer & Sons, Lahore, 1911 AD, p. 249, Formulation Id: AN2/230G, Formulation Name: Zimaad-e-Jaifal Barae Jild Ke Daag Dhabbe, Publication (Prior art):p. No. 08, English Translation including Terminology Conversion (TKDL Extracts): p. No. 09.

Mohammad Najmul Ghani Khan; Khazaain-al-Advia, vol. II (20th century AD), Nadeem Yunus Printer / Sheikh Mohd Basheer & Sons, Lahore, 1911 AD, p. 250, Formulation Id: AN2/230L1, Formulation Name: Roghan-e-Jaiphal, Publication (Prior art):p. No. 12, English Translation Including Terminology Conversion (TKDL Extracts): p. No. 13.

(Continued)

*Primary Examiner* — Shengjun Wang
*Assistant Examiner* — Jody Karol
(74) *Attorney, Agent, or Firm* — Mintz Levin Cohn Ferris Glovsky and Popeo, P.C.; Kongsik Kim (57) ABSTRACT The present invention relates to a new use of lignan-type compounds or an extract of nutmeg or aril of nutmeg comprising the same. More particularly, the present invention relates to a composition for skin whitening comprising a lignan-type compound or an extract of nutmeg or aril of nutmeg comprising the same. Because the lignan compound represented by Chemical Formulas 1 to 3 or the extract of nutmeg or aril of nutmeg has superior skin whitening activity by inhibiting melanin production and tyrosinase activity, it can be used for the preparation of a cosmetic composition, food composition or pharmaceutical composition for skin whitening.

1 Claim, 4 Drawing Sheets (56) References Cited

OTHER PUBLICATIONS

Mohammad Najmul Ghani Khan; Khazaain-al-Advia, vol. I (20th century AD), Nadeem Yunus Printer / Sheikh Mohd Basheer & Sons, Lahore, 1911 AD, p. 923, Formulation Id: NA2/490F, Formulation Name: Dawa-e-Husn, Publication (Prior art):p. No. 14, English Translation including Terminology Conversion (TKDL Extracts): p. No. 15.

Sodhala; Gadanigrahah ed,Ganga Sahaya Pandeya & Com.—Indradeva Tripathi,Part-3(Salakya-Pancakarma Khanda) Chaukhamba Sanskrit Sansthan(Varanasi) Ed. 3rd 1999 p. 388, Formulation Id: RG/948B, Formulation Name: Vyanga Cikitsa, Publication (Prior art):p. No. 18, English Translation including Terminology Conversion (TKDL Extracts): p. No. 19.

Kap-Joon Kim, et al., Yakhak Hoeji, vol. 46(2), 98-101 (2002).

Matsuda et al "Melanogenesis Stimulation in Murine B16 Melanoma Cells by *Piper nigrum* Leaf Extract and Its Lignan Constituents." *Biol. Pharm. Bull.* 27(10) 1611-1616 (2004).

Hirata et al "Mechanism of the melanogenesis stimulation activity of (-)-cubebin in murine BI6 melanoma cells." *Bioorganic & Medicinal Chemistry.* 15 (2007) 4897-4902.

Latha, P.G. et al., "Pharmacology and chemistry of *Myristica fragrans* Houtt.—a review", Journal of Spices and Aromatic Crops, vol. 14(2) : 94-101 (2005).

Gupta, A.D. et al., "Chemistry, antioxidant and antimicrobial potential of nutmeg (*Myristica fragrans* Houtt)", Journal of Genetic Engineering and Biotechnology 11, 25-31 (2013).

N.K. Leela, "Nutmeg and Mace", Section 9, *Chemistry of Spices* (2008).

G. Simpson et al., "Comparison of the Chemical Composition of East Indian, Jamaican and Other West Indian Essential Oils of *Myristica fragrans* Houtt.", Journal of Essential Oil Research, 14:1, 6-9 (2002).

* cited by examiner

USE OF LIGNAN-TYPE COMPOUNDS OR EXTRACT OF NUTMEG OR ARIL OF NUTMEG COMPRISING THE SAME

TECHNICAL FIELD

This application claims priority based on Korean Patent Application No. 2007-0104783, filed on Oct. 17, 2007, the entire contents of which are incorporated herein by reference.

The present invention relates to a novel use of lignan-type compounds or an extract of nutmeg or aril of nutmeg comprising the same. More particularly, the present invention relates to a composition for skin whitening comprising a lignan-type compound or an extract of nutmeg or aril of nutmeg comprising the same.

BACKGROUND ART

Human skin color is determined by various factors, including the activity of melanocytes which produce the melanin pigment, distribution of blood vessels, skin thickness, presence or absence of pigments such as carotenoids and bilirubin, or the like. Of the factors, the dark pigment melanin which is produced from melanocytes by the action of many enzymes including tyrosinase is the most important.

The production of melanin is affected by genetic factors, physiological factors such as hormones, stress, etc. and environmental factors such as UV. Existing in the epidermis, the outermost skin layer, melanin protects the skin below from UV, etc. and reduces the generation of free radicals, thereby protecting proteins and genes in the skin. However, excessive production of melanin leads to the formation of chloasma, freckles, etc. as well as accelerating skin aging and inducing skin cancer.

From long ago, ascorbic acid, kojic acid, arbutin, hydroquinone, glutathione, their derivatives, or compounds having tyrosinase inhibition activity have been used in cosmetics or drugs in order to treat or ameliorate anomalous skin pigmentation such as chloasma, freckles, pigmentation, etc. and excessive melanin pigmentation caused by exposure to UV. However, their use is restricted because of insufficient skin whitening effect, safety issue on skin, formulation instability when used in cosmetics, or the like. Thus, researches are under way on natural substances having superior safety and excellent skin whitening activity.

Meanwhile, the nutmeg is a nut of *Myristica fragrans* which is a perennial plant cultured in tropical regions, and has been used as spices for a long time. In addition, the extract of the aril of nutmeg is peel region of the said fruit of *Myristica fragrans* and is reported that it has inhibition of proliferation of *Helicobacter pylori* (In Vivo., 17;541-4, 2003), activation of detoxification in liver (*Food Chem. Toxicol.*, 31;517-21, 1993), chemical prevention of skin verruca (*Cancer Lett.*, 56;59-63, 1991), anti-inflammation activity (*Jpn. J. Pharmacol.*, 49;155-63, 1999). However, the relationship between the nutmeg or the aril of nutmeg and skin whitening activity has never been reported as yet.

Particularly, macelignan extracted from said nutmeg or the extract of the aril of nutmeg is a representative lignan-type compound (*Phytochemistry*, 59: 169-173, 2002), and it has activity promoting activation of caspase-3 which induces apoptosis (*Biol. Pharm. Bull.*, 27: 1305-1307, 2004), antibacterial activity in oral microorganism (Korean Patent Publication Bulletin No. 10-691792), antiinflammation activity (Korean Patent Publication Bulletin No. 10-0579752), antiacne activity (Korean Patent Publication Bulletin No. 10-0567431), activity inhibiting lipid hyperoxidation of brain cell and active oxigen generation (*Biochem. Biophys. Res. Commu.*, 331: 1264-1269). However, there is still no report whether the austrobailignan 7 or licarin E which could be extracted from the nutmeg or the extract of the aril of nutmeg as well as the said macelignan has skin whitening activity or not.

DISCLOSURE

Technical Problem

The inventors of the present invention have researched on natural substances having skin whitening activity. We found out that lignan-type compounds or an extract of nutmeg or aril of nutmeg comprising the same have superior skin whitening activity and accomplished the present invention.

Accordingly, in an aspect, the present invention provides a cosmetic composition for skin whitening comprising a lignan-type compound selected from the group consisting of the compounds represented by the following Chemical Formulas 1 to 3 or an extract of nutmeg or aril of nutmeg comprising the same:

<Chemical Formula 1>

<Chemical Formula 2>

<Chemical Formula 3>

In another aspect, the present invention provides a food composition for skin whitening comprising a lignan-type compound selected from the group consisting of the compounds represented by Chemical Formulas 1 to 3 or an extract of nutmeg or aril of nutmeg comprising the same.

In another aspect, the present invention provides a pharmaceutical composition for skin whitening comprising a lignan-type compound selected from the group consisting of the compounds represented by Chemical Formulas 1 to 3 or an extract of nutmeg or aril of nutmeg comprising the same.

In another aspect, the present invention provides a use of a lignan-type compound selected from the group consisting of the compounds represented by Chemical Formulas 1 to 3 or an extract of nutmeg or aril of nutmeg comprising the same for the preparation of a cosmetic composition.

In another aspect, the present invention provides a use of a lignan-type compound selected from the group consisting of the compounds represented by Chemical Formulas 1 to 3 or an extract of nutmeg or aril of nutmeg comprising the same for the preparation of a food composition.

In another aspect, the present invention provides a use of a lignan-type compound selected from the group consisting of the compounds represented by Chemical Formulas 1 to 3 or an extract of nutmeg or aril of nutmeg comprising the same for the preparation of pharmaceutical composition.

In another aspect, the present invention provides a method for the inhibition of melanin production using a lignan-type compound selected from the group consisting of the compounds represented by Chemical Formulas 1 to 3 or an extract of nutmeg or aril of nutmeg comprising the same.

In another aspect, the present invention provides a method for the inhibition of tyrosinase activity using a lignan-type compound selected from the group consisting of the compounds represented by Chemical Formulas 1 to 3 or an extract of nutmeg or aril of nutmeg comprising the same.

Technical Solution

To achieve the above objects, the present invention provides a cosmetic composition for skin whitening comprising a lignan-type compound selected from the group consisting of the compounds represented by the following Chemical Formulas 1 to 3 or an extract of nutmeg or aril of nutmeg comprising the same:

<Chemical Formula 1>

<Chemical Formula 2>

<Chemical Formula 3>

In another aspect, the present invention provides a food composition for skin whitening comprising a lignan-type compound selected from the group consisting of the compounds represented by Chemical Formulas 1 to 3 or an extract of nutmeg or aril of nutmeg comprising the same.

The present invention provides a pharmaceutical composition for skin whitening comprising a lignan-type compound selected from the group consisting of the compounds represented by Chemical Formulas 1 to 3 or an extract of nutmeg or aril of nutmeg comprising the same.

The present invention provides a use of a lignan-type compound selected from the group consisting of the compounds represented by Chemical Formulas 1 to 3 or an extract of nutmeg or aril of nutmeg comprising the same for the preparation of a cosmetic composition.

The present invention provides a use of a lignan-type compound selected from the group consisting of the compounds represented by Chemical Formulas 1 to 3 or an extract of nutmeg or aril of nutmeg comprising the same for the preparation of a food composition.

The present invention provides a use of a lignan-type compound selected from the group consisting of the compounds represented by Chemical Formulas 1 to 3 or an extract of nutmeg or aril of nutmeg comprising the same for the preparation of a pharmaceutical composition.

The present invention provides a method for the inhibition of melanin production using a lignan-type compound selected from the group consisting of the compounds represented by Chemical Formulas 1 to 3 or an extract of nutmeg or aril of nutmeg comprising the same.

The present invention provides a method for the inhibition of tyrosinase activity using a lignan-type compound selected from the group consisting of the compounds represented by Chemical Formulas 1 to 3 or an extract of nutmeg or aril of nutmeg comprising the same.

Hereafter, the present invention will be described in detail.

'The nutmeg' of the present invention is a nut of *Myristica fragrans* which is a perennial plant cultured in tropical regions, and 'the aril of nutmeg' of the present invention is peel region of the said fruit of *Myristica fragrans*.

'The extract of nutmeg or aril of nutmeg' of the present invention refers to the extract comprising lignan-type compound originated from the nutmeg or the aril of nutmeg. The method for preparing the extract of the nutmeg or the extract of the aril of nutmeg is not specially limited thereto, if comprising the lignan-type compound. Preferably, it may be prepared from the nutmeg or the aril of nutmeg by extracting with at least one solvent selected from the group consisting of water, C1-C6 organic solvent and subcritical or supercritical fluid. If necessary, a process of filtration or condensation commonly used in the related art may be further added.

The C1-C6 organic solvent may be selected from C1-C6 alcohol, acetone, ether, benzene, chloroform, ethyl acetate, methylene chloride, hexane, cyclohexane and petroleum ether, but not limited thereto.

As used herein, the "supercritical fluid" refers to any substance being gas at general conditions but fluid at a temperature and pressure above its thermodynamic critical point. The "subcritical fluid" includes subcritical liquid and gas. Especially, the subcritical liquid refers to a fluid at temperatures below the supercritical temperature and the saturation temperature. And, the subcritical gas refers to a fluid at temperatures above the saturation temperature and pressures below the supercritical pressure. The supercritical fluid and subcritical fluid are used in various fields, including pharmaceutical industry, food industry, cosmetics/perfume industry, chemical industry and energy industry. The supercritical fluid and subcritical fluid that may be used in the present invention are not specially limited. For example, carbon dioxide, nitrogen, nitrous oxide, methane, ethylene, propane, propylene, petroleum ether, ethyl ether, cyclohexane, etc. may be used. Especially, carbon dioxide is preferred because it is easily available, relatively inexpensive, inexplosive, and sufficiently safe for processing. Carbon dioxide has a critical temperature of 31.1° C. and a critical pressure of 73.8 atm.

As an embodiment of the present invention, dry the nutmeg or the aril of nutmeg was ground, extracted using ethanol, hexane or chloroform solvent, filtered and concentrated to prepare an ethanol, hexane or chloroform extract of the nutmeg or the aril of nutmeg. Further, the nutmeg was added to a supercritical fluid extractor using carbon dioxide ($CO_2$) as supercritical fluid to prepare a supercritical extract of the nutmeg (see Example 1).

As used herein, the "lignan-type compound" refers to a compound selected from the group consisting of the compounds represented by the following Chemical Formulas 1 to 3. Specifically, the compound represented by Chemical Formula 1 is (macelignan, 4-((2S,3R)-4-Benzo[1,3]dioxol-5-yl-2,3-dimethyl-butyl)-2-methoxyphenol), the compound represented by Chemical Formula 2 is austobailignan 7 (4-(1-Benzo[1,3]dioxol-5-yl-2-methyl-butoxymethyl)-2-methoxy-phenol, and the compound represented by Chemical Formula 3 is licarin E(5-(7-Methoxy-3-methyl-5-propenyl-2,3-dihydro-benzofuran-2-yl)-benzo[1,3]dioxole).

<Chemical Formula 1>

<Chemical Formula 2>

<Chemical Formula 3>

The lignan-type compound may be prepared according to a known synthesis method or may be obtained extracting from the said the nutmeg or the aril of nutmeg, isolating and purifying thereof. For the isolation and purification of lignan-type compound from the nutmeg or the aril of nutmeg, column chromatography or high-performance liquid chromatography (HPLC) using silica gel, activated alumina or various other synthetic resins may be used alone or in combination, although not limited thereto.

As an embodiment of the present invention, the said macelignan, austobilignan 7, or licarin E was isolated from the extract of dry nutmeg or aril of nutmeg by using well known silica gel column chromatography (see Examples 2).

A lignan-type compound selected from the group consisting of the compounds represented by Chemical Formulas 1 to 3 or an extract of nutmeg or aril of nutmeg comprising the same has superior skin whitening activity.

Specifically, when added to Melan-a cells (melanocytes), the lignan-type compound or the nutmeg extract or the nutmeg aril extract comprising the same remarkably inhibited melanin production (see Test Example 1), inhibited the activity of tyrosinase, which is involved in melanin production (see Test Example 2), and inhibited the expression of tyrosinase and tyrosinase-related proteins (TRP-1, TRP-2) (see Test Example 3).

Accordingly, the lignan-type compound or the nutmeg extract or the nutmeg aril extract comprising the same can be used as an effective ingredient of a cosmetic composition, food composition or pharmaceutical composition for skin whitening.

A composition for cosmetics of the present invention contains the lignan-type compound selected from the group consisting of the compound represented by Chemical Formulas 1 to 3 or the extract of nutmeg or aril of nutmeg comprising the same as an effective component, and may be prepared in the form of basic cosmetics (lotions, cream, essence, cleansers such as cleansing foam and cleansing water, pack, body oil), coloring cosmetics (foundation, lip-stick, mascara, make-up base), hair care composition (shampoo, rinse, hair conditioner, hair gel) and soap with dermatologically acceptable excipients.

The said excipients may comprise, but not limited thereto, skin softener, skin infiltration enhancer, colorant, odorant, emulsifier, thickener, or solvent. In addition, it is possible to add fragrance, a pigment, bactericidal agent, an antioxidant, a preservative, moisturizer and the like, and to add thickening agents, inorganic salts or synthetic polymers for improving physical properties. For example, in case of manufacturing a cleanser and soap comprising the composition of the present invention, they may be prepared easily by adding the lignan-type compound selected from the group consisting of the compound represented by Chemical Formulas 1 to 3 or the extract of nutmeg or aril nutmeg comprising the same to conventional cleanser or soap base. In case of manufacturing a cream, it may be prepared by adding the lignan-type compound selected from the group consisting of the compound represented by Chemical Formulas 1 to 3 or the extract of nutmeg or aril of nutmeg comprising the same to conventional oil-in-water cream base. In addition, it is possible to add a fragrance, a chelating agent, a pigment, an antioxidant, a preservative, and the like, and to add synthetic or natural proteins, minerals or vitamins for improving physical properties.

The lignan-type compound or the extract of nutmeg or aril of nutmeg comprising the same of the present invention may be preferably comprised by the form of composition for cosmetics in the range of 0.001-10 wt %, and more preferably 0.01-5 wt %, based on the total weight of a formulation. If the composition is added in an amount of less than 0.001 wt %, it will provide low effect in skin whitening effect, and if it is added in an amount of more than 10 wt %, it will have difficulty in safety or formulation.

Meanwhile, the composition for food of the present invention may comprise all kinds of forms including functional food, nutritional supplement, health food, and food additives.

The said composition for food may be prepared into various kinds of forms by the methods known in the art. For example, as a health food, the lignan-type compound or the extract of nutmeg or aril of nutmeg of the present invention may be prepared into tea, juice, and drink for drinking or may be prepared into liquefaction, granules, capsules, or powder for uptake. Also, conventional active ingredient which is well known as having activity in skin whitening may be mixed with the lignan-type compound or the extract of nutmeg or aril of nutmeg of the present invention so as to prepare a composition. Also, for preparing functional foods, the lignan-type compound or the extract of nutmeg or aril of nutmeg of the present invention may be added to beverages (including alcoholic beverages), fruits, and their processed foods (e.g. canned fruit, bottled fruit, jam, marmalade etc.), fishes, meats, and their processed foods (e.g. ham, sausage, corn beef etc.), breads and noodles (e.g. Japanese noodle, buckwheat noodle, Chinese noodle, spaghetti, macaroni etc.), fruit juice, drinks, cookies, toffee, dairy products (e.g. butter, cheese etc.), vegetable oil, margarine, vegetable protein, retort food, frozen food, various seasonings (e.g. soybean paste, soybean sauce, sauce etc.). In addition, the lignan-type compound or the extract of nutmeg or aril of nutmeg may be prepared in a form of powder or extract for food additives.

The lignan-type compound or the extract of nutmeg or aril of nutmeg of the present invention may be properly comprised by the form of composition for food preferably in the range of 0.01 to 50% based on the total weight of a food. More preferably, a food composition of the present invention may be prepared particularly mixing conventional active ingredient which is well known as having activity in skin whitening with the lignan-type compound or the extract of nutmeg or aril of nutmeg of the present invention.

Meanwhile, a pharmaceutical composition of the present invention may comprise the lignan-type compound or the extract of nutmeg or aril of nutmeg alone or together with one or more carrier, excipient, or diluent additionaly. A pharmaceutically acceptable carrier, for example, carriers for the parenteral or oral preparations may be included. The carriers for the oral preparations may comprise lactose, starch, cellulose derivatives, magnesium stearate, stearic acid. In addition, the carriers for the parenteral preparations may comprise water, oil, saline, aqueous glucose and glycol, and stabilizers and preservatives. The examples of the stabilizers may be antioxidant such as sodium hydrogen sulfite, sodium sulfite, and ascorbic acid. The examples of the preservatives may be benzalkonium chloride, methyl- or prophyl-paraben, and chlorobutanol. The list of pharmaceutically acceptable carriers are disclosed in Remington's Pharmaceutical Sciences, 19th ed., Mack Publishing Company, Easton, Pa., 1995.

The inventive pharmaceutical composition may be administered to mammalians including human beings by various routes. For example, it may be administered by oral or parenteral preparation. A parenteral preparation may be, but not limited thereto, intravenous, intramuscular, intraarterial, intramarrow, subdural, intracardiac, intracutaneous, subcutaneous, intraperitoneal, intranasal, gastrointestinal tracts, parenteral, sublingual or rectum. A pharmaceutical composition of the present invention may be formulated in the form of oral preparation or parenteral preparation according to the described above. In case of the formulation for oral administraion, the composition of the present invention may be formulated into powders, granules, tablets, pills, and sugar-coated tablets, capsules, liquids, gels, syrups, slurries, and emulsions by the method well known in the art. For example, preparations for oral administration may be harvested in the form of tablets or sugar-coated tablets by mixing an effective component with a solid excipient, grinding, and adding appropriate supplemental agents, then manufacturing a form of granular mixture. For examples of appropriate excipient, it may comprise sugars comprising lactose, dextrose, sucrose, sorbitol, mannitol, xylitol, erythritol and maltitol, starches comprising corn starch, wheat starch, rice starch and potato starch, celluloses comprising cellulose, methyl cellulose, sodium carboxymethylcellulose and hydroxypropylmethylcellulose, and fillers comprising gelatin and polyvinylpyrrolidone. And, if desired, it may comprise cross-linked polyvinylpyrrolidone, agar, alginic acid or sodium alginate as a solutionizer. Further, the inventive pharmaceutical composition may comprise anti-coagulant, lubricant, wetting agents, flavors, emulsifying agents and antiseptics additionally. In case of pharmaceutical formulations for parenteral administration, it may be prepared in the forms of injectable preparations, creams, lotions, ointments, oils, humectant, gels, aerosol, and nasal inhalations by the method well known in the art. The formulation of the above-mentioned is well described in Remington's Pharmaceutical Science, 15th Edition, 1975. Mack Publishing Company, Easton, Pa. 18042, Chapter 87: Blaug, Seymour which is well known prescription book.

Total effective amount of pharmaceutical composition of the present invention may be administered to a patient with a single dose, or may be administered with multiple doses by fractionated treatment protocol. The pharmaceutical composition of the present invention may contain variable amount of effective ingredient according to the disease severity. In case of parenteral administration, the effective amount of the lignan-type compound or the extract of nutmeg or aril of nutmeg comprising the same is preferably about 0.01 to 50 mg/kg body weight/day, more preferably 0.1 to 30 mg/kg body weight/day, and, in case of oral administration, the effective amount of the inventive composition is preferably about 0.01 to 100 mg/kg body weight/day, more preferably 0.1 to 50 mg/kg body weight/day with a single dose or multiple doses. However, the dose of the lignan-type compound or the extract of nutmeg or aril of nutmeg may be suitably determined by considering various factors, such as age, body weight, health condition, sex, disease severity, diet and excretion of a subject in need of treatment, as well as administration time and administration route. When those are considered, skilled person in the art may determine appropriate dose of the lignan-type compound or the extract of nutmeg or aril of nutmeg for a certain use for the skin whitening activity. The inventive pharmaceutical composition may not limit formulations, administration routes, and administration methods as long as they show the effect of the present invention.

Further, because the lignan-type compound represented by Chemical Formulas 1 to 3 or the extract of nutmeg or aril of nutmeg has superior skin whitening activity, it can be used for the preparation of a cosmetic composition, food composition or pharmaceutical composition for skin whitening activity.

The method for preparing the cosmetic composition, food composition or pharmaceutical composition using the lignan-type compound or the extract of nutmeg or aril of nutmeg is the same as described above. And, the amount of the lignan-type compound or the extract of nutmeg or aril of nutmeg in the compositions is the same as described above.

Further, the lignan-type compound selected from the group consisting of the compound represented by Chemical Formulas 1 to 3 or the extract of nutmeg or aril of nutmeg may be used in a method for inhibition of melanin production and inhibition of tyrosinase activity.

For inhibition of melanin production and inhibition of tyrosinase activity, the lignan-type compound or the extract of nutmeg or aril of nutmeg may be administered to a subject in need thereof with an effective amount.

As used herein, the "subject in need" refers to a mammal, preferably a human, in need of skin whitening by inhibition of melanin production and inhibition of tyrosinase activity. And, the "effective amount" refers to an amount which exhibits the effect of skin whitening by inhibition of melanin production and inhibition of tyrosinase activity in the subject. The administration method and administration dose for administering with the effective amount are the same as described in detail above.

Advantageous Effects

As can be seen from the foregoing, the lignan-type compound selected from the group consisting of the compound represented by Chemical Formulas 1 to 3 or the extract of nutmeg or aril of nutmeg inhibits melanin production and tyrosinase activity, therefore has excellent effect on skin whitening. Accordingly, it may be useful for an effective ingredient in cosmetic, food, or pharmaceutical composition for skin whitening.

MODE FOR INVENTION

Hereinafter, the constitution and effect of the present invention will be described in detail through examples. However, the following examples are given only for the purpose of illustrating the present invention, and the scope of the present invention is not limited by them.

Example 1

Preparation of Nutmeg or Nutmeg Aril Extract Having Skin Whitening Activity 1-1. Preparation of Nutmeg Extract Dry nutmeg was ground using a mixer. 100 g of the ground nutmeg sample was added to 1 L of ethanol and extracted at room temperature for 48 hours. The extracted sample was filtered through Whatman No. 2 filter paper. The solvent component was removed from the filtered extract solution by concentrating using a vacuum rotary evaporator. A nutmeg ethanol extract was obtained.

Further, a nutmeg methanol, hexane or chloroform extract was obtained in the same manner as above using methanol, hexane or chloroform as extraction solvent instead of ethanol.

Further, a nutmeg supercritical extract was prepared using a supercritical fluid extractor. Specifically, carbon dioxide ($CO_2$) was used as supercritical fluid. Extraction was carried out at 50° C. and 200 bar, and the solvent component was removed from the extract solution.

1-2. Preparation of Nutmeg Aril Extract

Dry aril of nutmeg was ground using a mixer. 100 g of the ground nutmeg aril sample was added to 1 L of ethanol and extracted at room temperature for 48 hours. A nutmeg aril ethanol extract was prepared in the same manner as Example 1-1.

Example 2

Preparation of Compounds Having Skin Whitening Activity from Nutmeg or Nutmeg Aril Extract 2-1. Isolation of Macelignan The concentrated nutmeg ethanol extract obtained in Example 1-1 was mixed with ethyl acetate. The ethyl acetate soluble component was extracted and ethyl acetate was removed to concentrate the ethyl acetate soluble component. Inactive components were removed using a column in which silica gel was packed with 6×15 cm, and using a solvent system consisting of hexane and ethyl acetate (10:1, v/v). Then, after fractionating using a solvent mixture of hexane and ethyl acetate (20:1, v/v), followed by elution using 80% methanol by Rp-18 column chromatography, macelignan [4-((2S,3R)-4-benzo[1,3]dioxol-5-yl-2,3-dimethyl-butyl)-2-methoxyphenol] of the following Chemical Formula 1 was isolated as a pure substance having skin whitening activity.

Chemical Formula 1

2-2. Isolation of Austrobailignan 7

The concentrated nutmeg aril ethanol extract obtained in Example 1-2 was fractionated using ethyl acetate, butanol and water. The ethyl acetate fraction (10.29 g) was eluted using a solvent mixture of chloroform and ethyl acetate (9:1, v/v) by silica gel column chromatography. Fraction V (0.52 g) and fraction VI (0.19 g) were obtained. Fraction VI was eluted using a solvent mixture of chloroform, ethyl acetate and acetone (30:1:2, v/v/v) by column chromatography. Fraction VI-B (0.52 g) was obtained. Finally, fraction VI-B was eluted using 100% methanol by recycling high-performance liquid chromatography (HPLC). 0.011 g of austrobailignan [7(4-(1-benzo[1,3]dioxol-5-yl-2-methyl-butoxymethyl)-2-methoxy-phenol)] of the following Chemical Formula 2 was isolated as a pure substance having skin whitening activity.

Chemical Formula 2

2-3. Isolation of Licarin E

The concentrated nutmeg aril ethanol extract obtained in Example 1-2 was fractionated using ethyl acetate, butanol and water. The ethyl acetate fraction (18.44 g) was eluted using a solvent mixture of chloroform and ethyl acetate (9:1, v/v) by silica gel column chromatography. Fraction II (3.04 g) was obtained. Fraction II was eluted using a solvent mixture of chloroform, hexane, ethyl acetate and acetone (15:10:0.1:0.1, v/v/v/v) by column chromatography. Fraction II-B (0.4 g) was obtained. Finally, fraction II-B, was eluted using 100% methanol by recycling HPLC. 0.016 g of licarin E [5-(7-methoxy-3-methyl-5-propenyl-2,3-dihydro-benzofuran-2-yl)-benzo[1,3]dioxole] of the following Chemical Formula 3 was isolated as a pure substance having skin whitening activity.

Chemical Formula 3

Test Example 1

Melanin Production Inhibition Activity 1-1. Melanin Production Inhibition Activity of Nutmeg or Nutmeg Aril Extract Melanin production inhibition activity of the nutmeg ethanol extract prepared in Example 1-1 was investigated.

Figure 1:
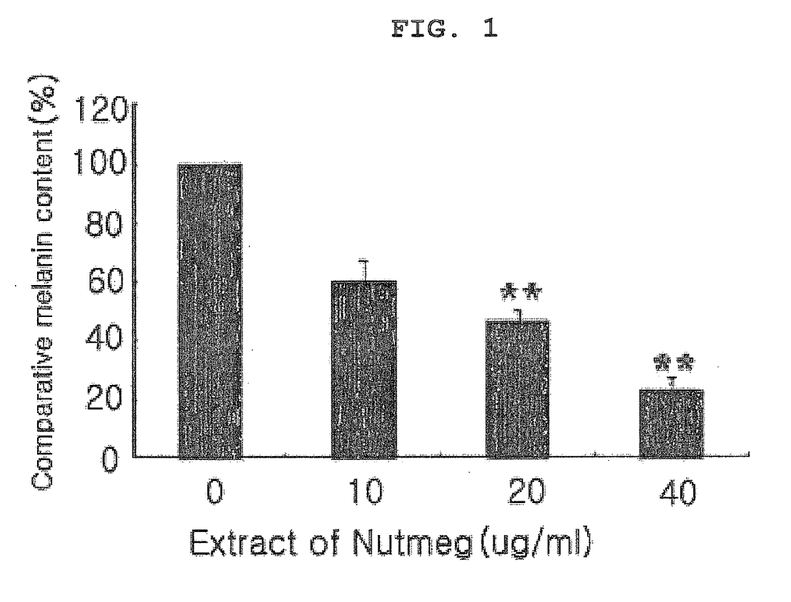
FIG. 1 shows the melanin production inhibition activity of a nutmeg ethanol extract.

Specifically, Melan-a cells were placed on a 6-well plate (melanin quantitated) at a concentration of $2\times10^5$ cells/mL (final volume=3 mL) and cultured in a 10% $CO_2$ incubator (MCO-20AIC, Sanyo) at 37° C., using RPMI 1640 containing 10% FBS and 2 μM TPA (phorbol-12-myristate 13-acetate), for 24 hours. After removing the culture medium, the nutmeg ethanol extract prepared in Example 1-1 was added to RPMI 1640 medium and treated every day for 3 days. 5 days later, the culture medium was removed from the 6-well plate and, after treating with 0.25% trypsin-EDTA solution (Sigma Chemical Co.), cell pellets were collected and transferred to a 1.5 mL tube. After centrifuging at 10,000 rpm for 10 minutes, the supernatant was removed. Thus obtained pellets were dried at 60° C. and added to 100 μL of 1N NaOH in order to dissolve melanin contained in the cells. The solution was diluted with PBS and absorbance was measured at 475 nm using an ELISA reader. Melanin content was calculated according to the following Equation 1. The result is given in FIG. 1. The group to which the nutmeg ethanol extract was not used served as the control group.

$$\text{Melanin content relative to control group (\%)} = \frac{\text{Absorbance of test group}}{\text{Absorbance of control group}} \times 100 \quad \text{Equation 1}$$

As seen from FIG. 1, the nutmeg ethanol extract exhibited superior melanin production inhibition activity and thus is expected to provide excellent skin whitening effect (**: $P<0.01$).

Further, Melan-a cells were treated with 40 μg/mL of the nutmeg hexane extract, chloroform extract and supercritical extract prepared in Example 1-1 and the nutmeg aril ethanol extract prepared in Example 1-2, and the degree of melanin production was measured in the same manner as above. The nutmeg hexane extract, the nutmeg chloroform extract, the nutmeg supercritical extract and the nutmeg aril ethanol extract exhibited about 53.74%, about 66.93%, about 73.80% and about 70.50% of melanin production inhibition, respectively (not shown in the figure).

Accordingly, it can be seen that the nutmeg or nutmeg aril extract has superior melanin production inhibition activity and can be used as an effective component of a composition for skin whitening.

1-2. Melanin Production Inhibition Activity Macelignan, Austrobailignan 7 and Licarin E Melan-a cells were treated with the macelignan isolated in Example 2-1, and the degree of melanin production was measured in the same manner as Test Example 1-1. The result is given in FIG. 2.

Figure 2:
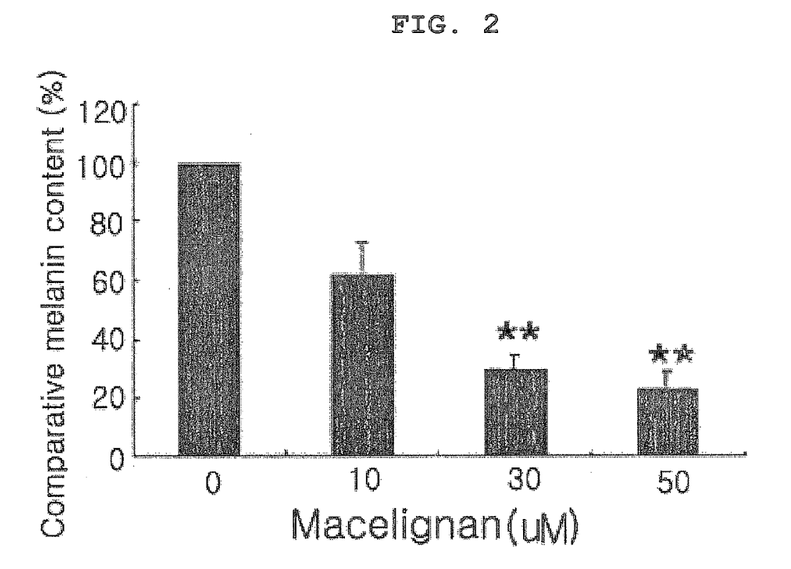
FIG. 2 shows the melanin production inhibition activity of macelignan.

As seen from FIG. 2, macelignan exhibited superior melanin production inhibition activity and thus is expected to provide excellent skin whitening effect (**: $P<0.01$).

Further, Melan-a cells were treated with the austrobailignan 7(750 μM) and licarin E (50 μM) isolated in Example 2, and the degree of melanin production was measured in the same manner as Test Example 1-1. Austrobailignan 7 and licarin E exhibited about 53.89% and about 58.44% of melanin production inhibition, respectively (not shown in the figure).

Accordingly, it can be seen that macelignan, austrobailignan 7 and licarin E have superior melanin production inhibition activity and can be used as an effective component of a composition for skin whitening.

Test Example 2

Tyrosinase Inhibition Activity 2-1. Tyrosinase Inhibition Activity of Nutmeg or Nutmeg Aril Extract It was investigated if the nutmeg ethanol extract prepared in Example 1-1 inhibits the activity of tyrosinase, which is involved in melanin production.

Melan-a cells were treated with the nutmeg ethanol extract prepared in Example 1-1 for 3 days, as in Test Example 1-1. 5 days later, the culture medium was removed from the 6-well plate and, after treating with 0.25% trypsin-EDTA solution (Sigma Chemical Co.), cell pellets were collected and transferred to a 1.5 mL tube. After adding 200 μL of phosphate buffer (pH 6.8) followed by centrifuging at 10,000 rpm for 10 minutes, the supernatant was collected. 150 μL of the supernatant was moved to a 96-well microplate and 50 μL of catechol was added. After culturing at 37° C. for 30 minutes, the amount of produced DOPA chrome was determined by measuring absorbance at 490 nm using a microplate reader. The result is given in FIG. 3.

Figure 3:
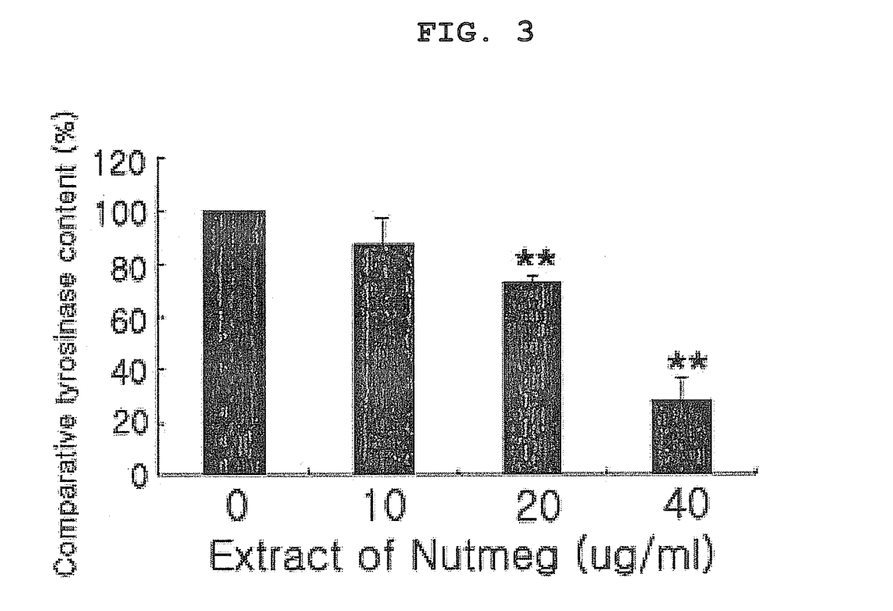
FIG. 3 shows the activity of inhibiting tyrosinase, which is involved in melanin production, of a nutmeg ethanol extract.

As seen from FIG. 3, treatment with the nutmeg ethanol extract prepared in Example 1-1 resulted in significantly reduced DOPA chrome production. Accordingly, considering that tyrosinase is an enzyme involved in the production of DOPA chrome, it can be seen that the nutmeg ethanol extract prepared in Example 1-1 can inhibit tyrosinase activity and thereby inhibit melanin production (**: P<0.01).

Further, Melan-a cells were treated with 40 μg/mL of the nutmeg hexane extract, chloroform extract and supercritical extract prepared in Example 1-1 and the nutmeg aril ethanol extract prepared in Example 1-2, and the degree of DOPA chrome production was measured in the same manner as above. The nutmeg hexane extract, the nutmeg chloroform extract, the nutmeg supercritical extract and the nutmeg aril ethanol extract exhibited about 54.92%, about 62.89%, about 68.34% and about 72.75% of melanin production inhibition, respectively (not shown in the figure).

2-2. Tyrosinase Inhibition Activity of Macelignan, Austrobailignan 7 and Licarin E Melan-a cells were treated with the macelignan isolated in Example 2-1, and the degree of DOPA chrome production was measured in the same manner as Test Example 2-1. The result is given in FIG. 4.

Figure 4:
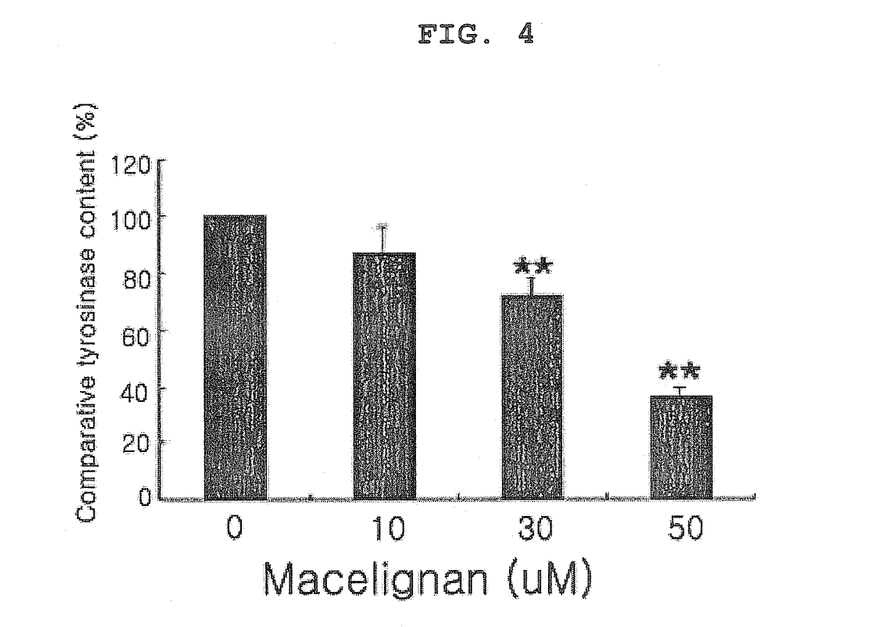
FIG. 4 shows the activity of inhibiting tyrosinase, which is involved in melanin production, of macelignan.

As seen from FIG. 4, macelignan exhibited superior DOPA chrome production inhibition activity and thus is expected to be able to inhibit tyrosinase activity (**: P<0.01).

Further, Melan-a cells were treated with the austrobailignan 7 and licarin E isolated in Example 2, and the degree of DOPA chrome production was measured in the same manner as Test Example 1-1. Austrobailignan 7 and licarin E exhibited about 54.87% and about 60.04% of DOPA chrome production inhibition, respectively (not shown in the figure).

Accordingly, considering that tyrosinase is an enzyme involved in DOPA chrome production, it can be seen that macelignan, austrobailignan 7 and licarin E can inhibit melanin production through inhibiting tyrosinase activity.

Test Example 3

Inhibition of Expression of Tyrosinase and Tyrosinase-Related Proteins (TRP-1, TRP-2)

3-1. Inhibition of Expression of Tyrosinase, TRP-1 and TRP-2 of Nutmeg Extract

Western blotting and Bradford protein assay were carried out in order to investigate if the nutmeg ethanol extract prepared in Example 1-1 inhibits the expression of tyrosinase, tyrosinase-related protein 1 (TRP-1) and tyrosinase-related proteins 2 (TRP-2).

Specifically, proteins were extracted from the cells treated in Test Example 1-1 with the nutmeg ethanol extract and subjected to electrophoresis in 10% SDS-polyacrylamide gel. Then, the proteins were transferred from the gel to a nitrocellulose membrane. After treating with 5% skim milk at room temperature for 1 hour, primary antibodies of tyrosinase, TRP-1 and TRP-2 diluted in 5% skim milk to 1:1000 were added and allowed to be incubated at room temperature for 2 hours. After the incubation, the membrane was washed with Tris-buffer saline Tween 20(TBST) twice, for 10 minutes per each, while shaking. Secondary antibodies which recognize the primary antibodies, diluted in 5% skim milk to 1:1000, were added and allowed to be incubated at room temperature for 1 hour. As for the primary antibodies, the membrane was washed with TBST three times, for 10 minutes per each, while shaking, and subjected to development by chemiluminescence. The result is given in FIG. 5.

Figure 5:
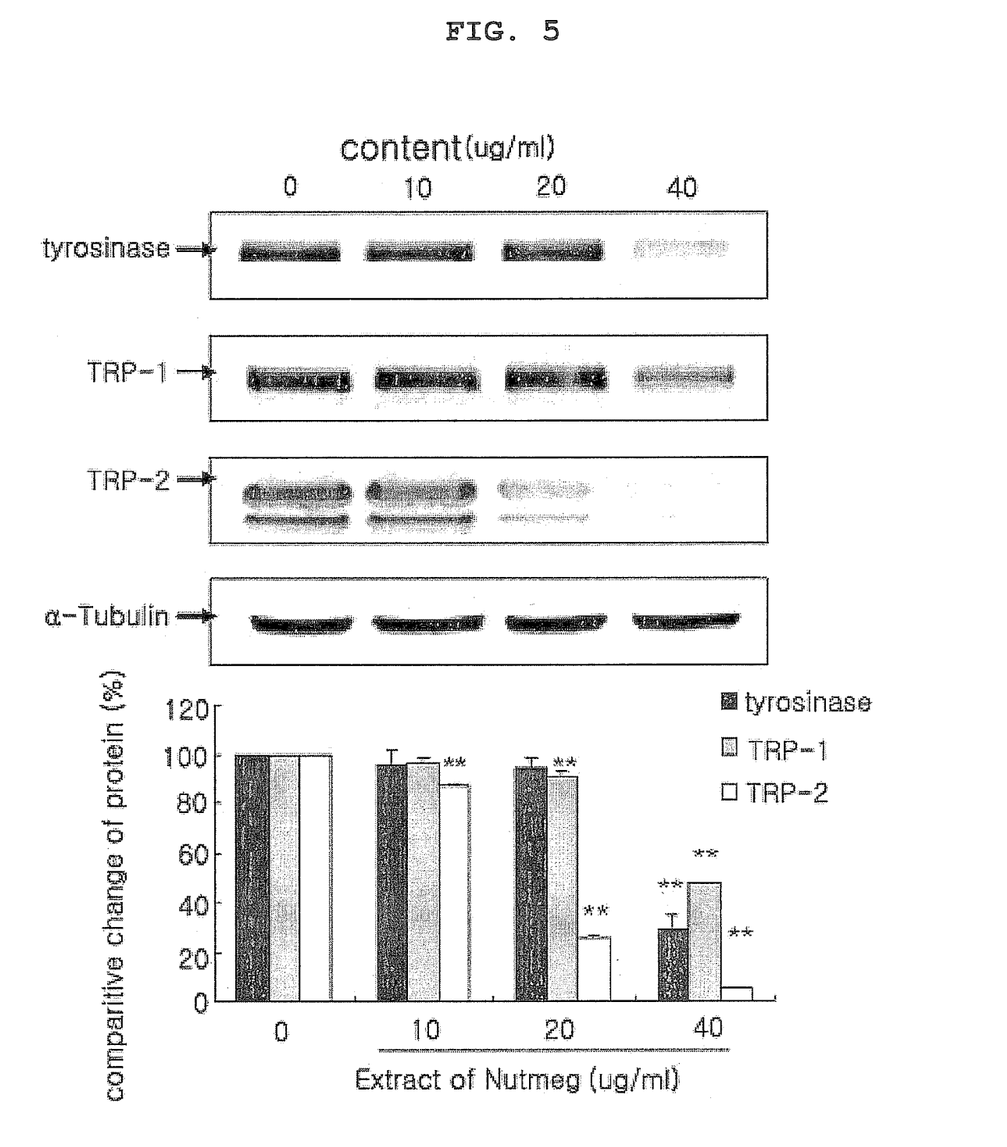
FIG. 5 shows the activity of inhibiting tyrosinase and tyrosinase-related proteins (TRP-1, TRP-2) of a nutmeg ethanol extract.

As seen from FIG. 5, the nutmeg ethanol extract could inhibit the expression of tyrosinase, TRP-1 and TRP-2 and thereby inhibit melanin production (**: P<0.01).

3-2. Inhibition of Expression of Tyrosinase, TRP-1 and TRP-2 of Macelignan

Melan-a cells were treated with the macelignan isolated in Example 2-1, and it was investigated if the expression of tyrosinase, TRP-1 and TRP-2 was inhibited, in the same manner as Test Example 3-1. The result is given in FIG. 6.

Figure 6:
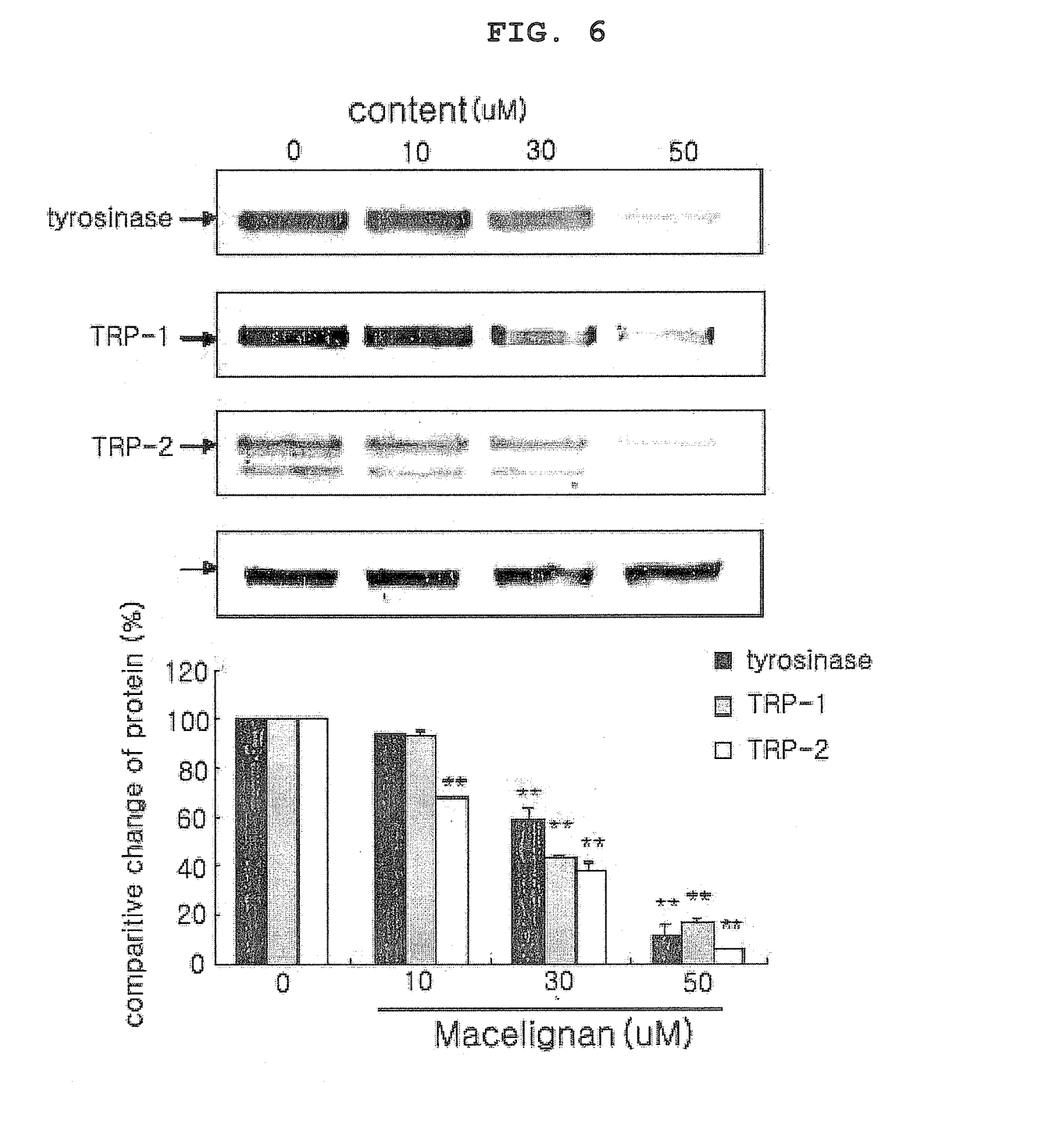
FIG. 6 shows the activity of inhibiting tyrosinase and tyrosinase-related proteins (TRP-1, TRP-2) of macelignan.

As seen from FIG. 6, macelignan could inhibit the expression of tyrosinase, TRP-1 and TRP-2 and thereby inhibit melanin production (**: P<0.01).

Formulation Example 1

Cosmetics 1-1 through 1-3. Nourishing Lotion (Milk Lotion)

Nourishing lotion was prepared according to method commonly used in the related art using the nutmeg extract or nutmeg aril extract prepared in Example 1 or the compounds isolated in Example 2(macelignan, austrobailignan 7 and licarin E), with the compositions of the following Table 1.

TABLE 1

| | Nourishing lotion | | |
|---|---|---|---|
| | Formulation Example 1-1 (wt %) | Formulation Example 1-2 (wt %) | Formulation Example 1-3 (wt %) |
| Compounds isolated in Example 2 | 2.0 | — | — |
| Nutmeg ethanol extract | — | 2.0 | — |
| Nutmeg aril ethanol extract | — | — | 2.0 |
| Squalene | 5.0 | 5.0 | 5.0 |
| Beeswax | 4.0 | 4.0 | 4.0 |
| Polysorbate 60 | 1.5 | 1.5 | 1.5 |
| Sorbitan sesquioleate | 1.5 | 1.5 | 1.5 |
| Liquid paraffin | 0.5 | 0.5 | 0.5 |
| Caprylic/capric triglyceride | 5.0 | 5.0 | 5.0 |
| Glycerine | 3.0 | 3.0 | 3.0 |
| Butylene glycol | 3.0 | 3.0 | 3.0 |
| Propylene glycol | 3.0 | 3.0 | 3.0 |
| Carboxyvinyl polymer | 0.1 | 0.1 | 0.1 |
| Triethanolamine | 0.2 | 0.2 | 0.2 |
| Antiseptic, pigment and perfume | adequate | adequate | adequate |
| Purified water | to 100 | to 100 | to 100 |

1-4 through 1-6. Softening Lotion (Skin Lotion)

Softening lotion was prepared according to a method commonly used in the related art using the nutmeg extract or nutmeg aril extract prepared in Example 1 or the compounds isolated in Example 2(macelignan, austrobailignan 7 and licarin E), with the compositions of the following Table 2.

TABLE 2

| | Softening lotion | | |
|---|---|---|---|
| | Formulation Example 1-4 (wt %) | Formulation Example 1-5 (wt %) | Formulation Example 1-6 (wt %) |
| Compounds isolated in Example 2 | 2.0 | — | — |

TABLE 2-continued

| Softening lotion | | | |
|---|---|---|---|
| | Formulation Example 1-4 (wt %) | Formulation Example 1-5 (wt %) | Formulation Example 1-6 (wt %) |
| Nutmeg ethanol extract | — | 2.0 | — |
| Nutmeg aril ethanol extract | — | — | 2.0 |
| Glycerine | 3.0 | 3.0 | 3.0 |
| Butylene glycol | 2.0 | 2.0 | 2.0 |
| Propylene glycol | 2.0 | 2.0 | 2.0 |
| Carboxyvinyl polymer | 0.1 | 0.1 | 0.1 |
| PEG 12 nonylphenyl ether | 0.2 | 0.2 | 0.2 |
| Polysorbate 80 | 0.4 | 0.4 | 0.4 |
| Ethanol | 10.0 | 10.0 | 10.0 |
| Triethanolamine | 0.1 | 0.1 | 0.1 |
| Antiseptic, pigment and perfume | adequate | adequate | adequate |
| Purified water | to 100 | to 100 | to 100 |

1-7 through 1-9. Nourishing Cream

Nourishing cream was prepared according to a method commonly used in the related art using the nutmeg extract or nutmeg aril extract prepared in Example 1 or the compounds isolated in Example 2 (macelignan, austrobailignan 7 and licarin E), with the compositions of the following Table 3.

TABLE 3

| Nourishing cream | | | |
|---|---|---|---|
| | Formulation Example 1-7 (wt %) | Formulation Example 1-8 (wt %) | Formulation Example 1-9 (wt %) |
| Compounds isolated in Example 2 | 2.0 | — | — |
| Nutmeg ethanol extract | — | 2.0 | — |
| Nutmeg aril ethanol extract | — | — | 2.0 |
| Polysorbate 60 | 1.5 | 1.5 | 1.5 |
| Sorbitan sesquioleate | 0.5 | 0.5 | 0.5 |
| PEG 60 hydrogenated castor oil | 2.0 | 2.0 | 2.0 |
| Liquid paraffin | 10 | 10 | 10 |
| Squalene | 5.0 | 5.0 | 5.0 |
| Caprylic/capric triglyceride | 5.0 | 5.0 | 5.0 |
| Glycerine | 5.0 | 5.0 | 5.0 |
| Butylene glycol | 3.0 | 3.0 | 3.0 |
| Propylene glycol | 3.0 | 3.0 | 3.0 |
| Triethanolamine | 0.2 | 0.2 | 0.2 |
| Antiseptic | adequate | adequate | adequate |
| Pigment | adequate | adequate | adequate |
| Perfume | adequate | adequate | adequate |
| Purified water | to 100 | to 100 | to 100 |

1-10 through 1-12. Massage Cream

Massage cream was prepared according to a method commonly used in the related art using the nutmeg extract or nutmeg aril extract prepared in Example 1 or the compounds isolated in Example 2 (macelignan, austrobailignan 7 and licarin E), with the compositions of the following Table 4.

TABLE 4

| Massage cream | | | |
|---|---|---|---|
| | Formulation Example 1-10 (wt %) | Formulation Example 1-11 (wt %) | Formulation Example 1-12 (wt %) |
| Compounds isolated in Example 2 | 1.0 | — | — |
| Nutmeg ethanol extract | — | 1.0 | — |
| Nutmeg aril ethanol extract | — | — | 1.0 |
| Beeswax | 10.0 | 10.0 | 10.0 |
| Polysorbate 60 | 1.5 | 1.5 | 1.5 |
| PEG 60 hydrogenated castor oil | 2.0 | 2.0 | 2.0 |
| Sorbitan sesquioleate | 0.8 | 0.8 | 0.8 |
| Liquid paraffin | 40.0 | 40.0 | 40.0 |
| Squalene | 5.0 | 5.0 | 5.0 |
| Caprylic/capric triglyceride | 4.0 | 4.0 | 4.0 |
| Glycerine | 5.0 | 5.0 | 5.0 |
| Butylene glycol | 3.0 | 3.0 | 3.0 |
| Propylene glycol | 3.0 | 3.0 | 3.0 |
| Triethanolamine | 0.2 | 0.2 | 0.2 |
| Antiseptic, pigment and perfume | adequate | adequate | adequate |
| Purified water | to 100 | to 100 | to 100 |

1-13 through 1-15. Pack

Pack was prepared according to a method commonly used in the related art using the nutmeg extract or nutmeg aril extract prepared in Example 1 or the compounds isolated in Example 2 (macelignan, austrobailignan 7 and licarin E), with the compositions of the following Table 5.

TABLE 5

| Pack | | | |
|---|---|---|---|
| | Formulation Example 1-13 (wt %) | Formulation Example 1-14 (wt %) | Formulation Example 1-15 (wt %) |
| Compounds isolated in Example 2 | 1.0 | — | — |
| Nutmeg ethanol extract | — | 1.0 | — |
| Nutmeg aril ethanol extract | — | — | 1.0 |
| Polyvinyl alcohol | 13.0 | 13.0 | 13.0 |
| Sodium carboxymethyl cellulose | 0.2 | 0.2 | 0.2 |
| Glycerine | 5.0 | 5.0 | 5.0 |
| Allantoin | 0.1 | 0.1 | 0.1 |
| Ethanol | 6.0 | 6.0 | 6.0 |
| PEG 12 nonylphenyl ether | 0.3 | 0.3 | 0.3 |
| Polysorbate 60 | 0.3 | 0.3 | 0.3 |
| Antiseptic, pigment and perfume | adequate | adequate | adequate |
| Purified water | to 100 | to 100 | to 100 |

1-16 through 1-18. Gel

Gel was prepared according to a method commonly used in the related art using the nutmeg extract or nutmeg aril extract prepared in Example 1 or the compounds isolated in Example 2 (macelignan, austrobailignan 7 and licarin E), with the compositions of the following Table 6.

TABLE 6

Gel

| | Formulation Example 1-16 (wt %) | Formulation Example 1-17 (wt %) | Formulation Example 1-18 (wt %) |
|---|---|---|---|
| Compounds isolated in Example 2 | 0.5 | — | — |
| Nutmeg ethanol extract | — | 0.5 | — |
| Nutmeg aril ethanol extract | — | — | 0.5 |
| Ethylenediamine sodium acetate | 0.05 | 0.05 | 0.05 |
| Glycerine | 5.0 | 5.0 | 5.0 |
| Carboxyvinyl polymer | 0.3 | 0.3 | 0.3 |
| ethanol | 5.0 | 5.0 | 5.0 |
| PEG 60 hydrogenated castor oil | 0.5 | 0.5 | 0.5 |
| Triethanolamine | 0.3 | 0.3 | 0.3 |
| Antiseptic, pigment and perfume | adequate | adequate | adequate |
| Purified water | to 100 | to 100 | to 100 |

Formulation Example 2

Foods 2-1. Health Food 1,000 mg of the nutmeg extract or nutmeg aril extract prepared in Example 1 or the compounds isolated in Example 2 (macelignan, austrobailignan 7 and licarin E) may be mixed with 70 μg of vitamin A acetate, 1.0 mg of vitamin E, 0.13 mg of vitamin $B_1$, 0.15 mg of vitamin $B_2$, 0.5 mg of vitamin $B_6$, 0.2 μg of vitamin $B_{12}$, 10 mg of vitamin C, 10 μg of biotin, 1.7 mg of nicotinamide, 50 μg of folic acid, 0.5 mg of calcium pantothenate, 1.75 mg of ferrous sulfate, 0.82 mg of zinc oxide, 25.3 mg of magnesium carbonate, 15 mg of monobasic potassium phosphate, 55 mg of dibasic calcium phosphate, 90 mg of potassium citrate, 100 mg of calcium carbonate and 24.8 mg of magnesium chloride. The mixing proportion may be changed differently. The mixture may be prepared into granules according to a method commonly used in the related art and may be used for the preparation of a health food composition according to a method commonly used in the related art.

2-2. Health Drink 1,000 mg of the nutmeg extract or nutmeg aril extract prepared in Example 1 or the compounds isolated in Example 2 (macelignan, austrobailignan 7 and licarin E) may be mixed with 1,000 mg of citric acid, 100 g of oligosaccharide, 2 g of plum extract and 1 g of taurine according to a method commonly used in the related art. Purified water may be added to a total volume of 900 mL. After heating at 85° C. for about 1 hour while stirring, the resultant solution may be filtered and collected in a sterilized 2 L container. After sealing and sterilization, it may be kept cold to prepare a health drink composition.

2-3. Chewing Gum 0.1 wt % of the nutmeg extract or nutmeg aril extract prepared in Example 1 or the compounds isolated in Example 2 (macelignan, austrobailignan 7 and licarin E) may be mixed with 20 wt % of gum base, 76.9 wt % of sugar, 1 wt % of perfume and 2 wt % of water according to a method commonly used in the related art to prepare chewing gum.

2-4. Candy 0.1 wt % of the nutmeg extract or nutmeg aril extract prepared in Example 1 or the compounds isolated in Example 2 (macelignan, austrobailignan 7 and licarin E) may be mixed with 60 wt % of sugar, 39.8 wt % of starch syrup and 0.1 wt % of perfume according to a method commonly used in the related art to prepare candy.

2-5. Biscuit 1 wt % of the nutmeg extract or nutmeg aril extract prepared in Example 1 or the compounds isolated in Example 2 (macelignan, austrobailignan 7 and licarin E) may be mixed with 25.59 wt % of hard wheat flour, 22.22 wt % of medium wheat flour, 4.80 wt % of refined sugar, 0.73 wt % of table salt, 0.78 wt % of glucose, 11.78 wt % of palm shortening, 1.54 wt % of ammonium, 0.17 wt % of baking soda, 0.16 wt % of sodium bisulfite, 1.45 wt % of rice flour, 0.0001 wt % of vitamin $B_1$, 0.0001 wt % of vitamin $B_2$, 0.04 wt % of milk flavor, 20.6998 wt % of water, 1.16 wt % of whole milk powder, 0.29 wt % of milk replacer, 0.03 wt % of monobasic calcium phosphate, 0.29 wt % of scattering salt and 7.27 wt % of spray-milk according to a method commonly used in the related art to prepare biscuit.

Formulation Example 3

Drugs 3-1. Powder 50 mg of the nutmeg extract or nutmeg aril extract prepared in Example 1 or the compounds isolated in Example 2 (macelignan, austrobailignan 7 and licarin E) may be mixed with 2 g of crystalline cellulose and put in an airtight pouch according to a method commonly used in the related art to prepare powder.

3-2. Tablet 50 mg of the nutmeg extract or nutmeg aril extract prepared in Example 1 or the compounds isolated in Example 2 (macelignan, austrobailignan 7 and licarin E) may be mixed with 400 mg of crystalline cellulose and 5 mg of magnesium stearate and prepared into tablet according to a method commonly used in the related art.

3-3. Capsule 30 mg of the nutmeg extract or nutmeg aril extract prepared in Example 1 or the compounds isolated in Example 2 (macelignan, austrobailignan 7 and licarin E) may be mixed with 100 mg of whey protein, 400 mg of crystalline cellulose and 6 mg of magnesium stearate and filled in a gelatin capsule according to a method commonly used in the related art to prepare capsule.

3-4. Injection

According to a method commonly used in the related art, active ingredients may be dissolved in distilled water for injection and pH may be adjusted to about 7.5. Then, 100 mg of the nutmeg aril extract prepared in Example 1 or the compounds isolated in Example 2 (macelignan, austrobailignan 7 and licarin E), distilled water for injection and pH adjuster may be mixed and filled in a 2 mL ampule and sterilized to prepare injection.

Application Example

Pigmentation inhibition effect of the nourishing lotion, softening lotion, nourishing cream, massage cream, pack and gel prepared in Formulation Examples 1-1 through 1-18 was evaluated as follows.

Twenty healthy men and women were selected. An aluminum foil with six holes having a diameter of 7 mm in two rows was attached on each forearm. At a distance of cm from the forearm, light was illuminated with an intensity of 60 J/cm² using 1000 W Oriel solar simulator. The test area was washed well with 70% ethanol aqueous solution before the light illumination. Following the illumination, the formulations prepared in Formulation Examples 1-1 through 1-18 were applied on the test area, three times a day. After 3 weeks of application, the degree of pigmentation was evaluated with naked eyes. Pigmentation inhibition effect as compared to the control group was evaluated as remarkable, effective or ineffective. Further, the occurrence of any side effects was observed. The result is given in the following Table 7.

TABLE 7

| Test substance | Pigmentation inhibition effect | | | |
| --- | --- | --- | --- | --- |
| | Remarkable | Effective | Ineffective | Side effects |
| Formulation Example 1 | 6 | 10 | 4 | 0 |
| Formulation Example 2 | 4 | 11 | 5 | 0 |
| Formulation Example 3 | 4 | 10 | 6 | 0 |
| Formulation Example 4 | 6 | 9 | 5 | 0 |
| Formulation Example 5 | 4 | 10 | 6 | 0 |
| Formulation Example 6 | 3 | 9 | 8 | 0 |
| Formulation Example 7 | 7 | 10 | 3 | 0 |
| Formulation Example 8 | 5 | 9 | 6 | 0 |
| Formulation Example 9 | 3 | 10 | 7 | 0 |
| Formulation Example 10 | 6 | 10 | 4 | 0 |
| Formulation Example 11 | 3 | 10 | 7 | 0 |
| Formulation Example 12 | 3 | 9 | 8 | 0 |
| Formulation Example 13 | 5 | 10 | 5 | 0 |
| Formulation Example 14 | 4 | 10 | 6 | 0 |
| Formulation Example 15 | 4 | 9 | 7 | 0 |
| Formulation Example 16 | 4 | 12 | 4 | 0 |
| Formulation Example 17 | 3 | 11 | 6 | 0 |
| Formulation Example 18 | 3 | 11 | 6 | 0 |

Figures are the number of people.

As seen from Table 7, the cosmetic compositions for skin whitening comprising the skin whitening components of the present invention exhibited skin whitening effect in at least 12 people out of 20 subjects.

INDUSTRIAL APPLICABILITY

Because the lignan compound represented by Chemical Formulas 1 to 3 or the extract of nutmeg or aril of nutmeg comprising the same has superior skin whitening activity by inhibiting melanin production and tyrosinase activity, it can be used for the preparation of a cosmetic composition, food composition or pharmaceutical composition for skin whitening activity.

The invention claimed is:

1. A method for inhibiting melanin production in a subject in need thereof comprising a step of administering to the subject a composition comprising an effective amount of isolated macelignan represented by Chemical Formula 1, or a pharmaceutically acceptable salt thereof <Chemical Formula 1> wherein the effective amount of macelignan or pharmaceutically acceptable salt thereof is 0.001-10 wt.% based on the weight of the composition.

* * * * *